(12) United States Patent
Chu et al.

(10) Patent No.: US 6,442,419 B1
(45) Date of Patent: Aug. 27, 2002

(54) INFRARED 3D SCANNING SYSTEM

(75) Inventors: Liang-Chien Chu, Taoyuan; Chih-Chi Chang, Hsinchu, both of (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 09/721,798

(22) Filed: Nov. 24, 2000

(30) Foreign Application Priority Data

Sep. 20, 2000 (CN) ........................................ 89119292 A

(51) Int. Cl.⁷ ................................................ A61B 5/00
(52) U.S. Cl. ..................... 600/474; 600/549; 250/316.1; 250/332; 250/334
(58) Field of Search ................................. 600/473–476, 600/478, 549; 250/316.1, 334, 332, 338.1, 339.04, 363.02

(56) References Cited

U.S. PATENT DOCUMENTS 5,999,842 A * 12/1999 Harrison et al. ............ 600/474
6,023,637 A * 2/2000 Liu et al. .................... 600/474
6,044,288 A * 3/2000 Wake et al. ................. 600/407

\* cited by examiner

*Primary Examiner*—Ruth S. Smith
(74) *Attorney, Agent, or Firm*—W. Wayne Liauh

(57) ABSTRACT

This specification discloses an infrared (IR) 3D scanning system and, more specifically, a 3D scanning system that utilizes a plurality of IR detectors to detect an object and computes the 3D shape and its 3D temperature distribution of the object through signal processing of the 3D thermal image construction.

15 Claims, 3 Drawing Sheets

INFRARED 3D SCANNING SYSTEM

BACKGROUND OF THE INVENTION

1. Field of Invention

The present invention relates to an infrared (IR) 3D scanning system for 3D scanning to construct the shape of an object and, more particularly, to a 3D scanning system that can detect the temperature distribution and construct the shape of an object.

2. Related Art

Photo-sensing technology has been widely applied in daily life. Fingerprint identification systems, vehicle speedometers, CD players, cameras and printers all utilize the photo-sensing technology. As to the medical system, the most famous one is the application of 3D human body scan. Most of the image captured heads of 3D human body scanners used today are the combination of a low-power visible light laser and a camera that does no harm to human bodies. When beams of laser light are used to scan a standing human body, the heights of the visible light laser and the camera are adjusted so as to scanning the whole body. While scanning, the reflected laser beams from the human body surface are collected. Through 3D shape construction and data integration editing software, the 3D profile of the human body can be obtained. Since the human body shape is often related to the age, diet, exercise habit, etc, the doctor can then determine the biological state of the patient using the data. Most diseases, however, are not apparently detected by looking at the outlook of the human body; therefore such 3D human body scanner does not help too much in medical diagnosis.

Developing a photo-sensing system that can provide more information for medical diagnosis is what we should endeavor ourselves to.

SUMMARY OF THE INVENTION

To solve the above problem. the present invention provides an IR 3D scanning system which primarily measures the surface temperature distribution and constructs the shape of an object.

According to the disclosed invention. the IR 3D scanning system comprises an IR detecting mechanism and a signal decoding mechanism. By having the IR detecting mechanism perform a 360-degree data extraction from an object and through the construction of image processing software in a master computer in the signal decoding mechanism and image output of a display unit, the 3D profile and temperature distribution of an object can be displayed.

BRIEF DESCRIPTION OF THE DRAWINGS

The present invention will become more fully understood from the detailed description given hereinbelow illustration only, and thus are not limitative of the present invention, and wherein.

In the various drawings, the same references relate to the same elements.

DETAILED DESCRIPTION OF THE INVENTION

Figure 1:
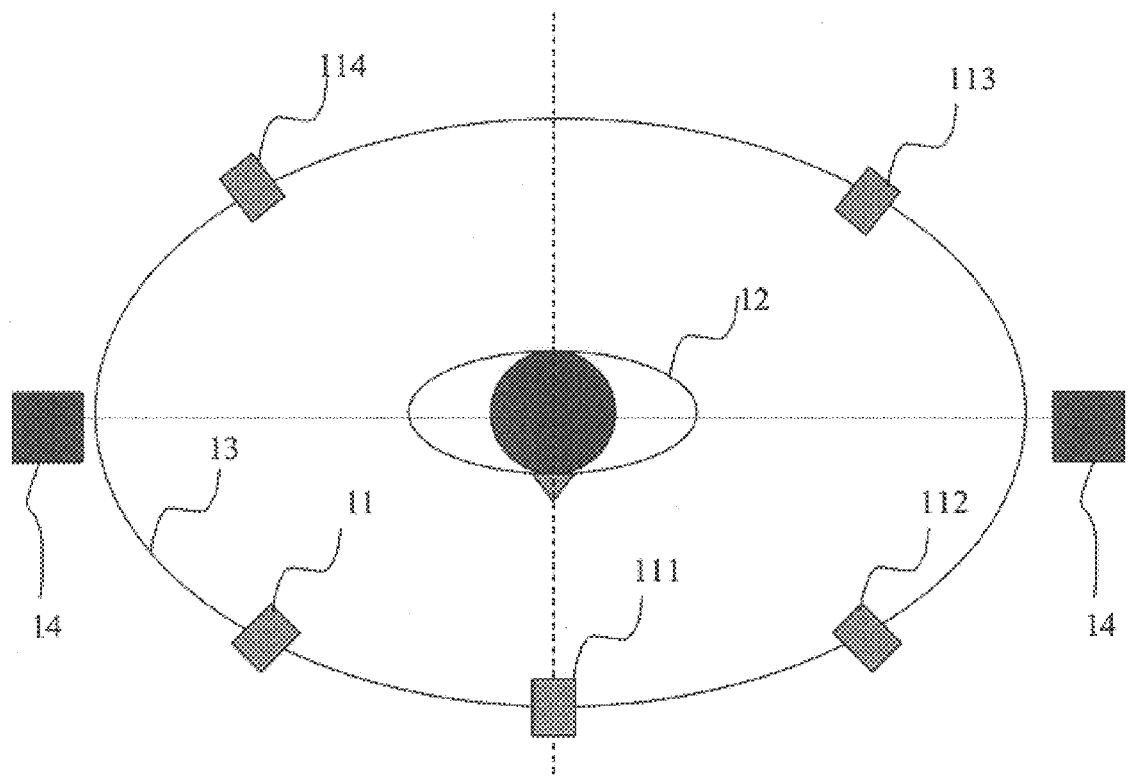
FIG. 1 is a top view of an IR detecting mechanism according to an embodiment of the disclosed IR 3D scanning system.

Please refer to FIG. 1, which is a top view of an IR detecting mechanism according to an embodiment of the disclosed IR 3D scanning system. The IR detecting mechanism comprises a plurality of IR detectors 11, 111, 112, 113, 114, a movable frame 13 and an axial pillar 14. The object 12 in the current embodiment is a human body. The movable frame 13 can be a ring structure or an arc structure for fixing the IR detectors. The number of IR detectors can be adjusted according to the complexity of the curved surface of the object 12 and the detector view angle limitation. Taking a mechanism with five IR detectors as an example, a first IR detector 11, a second IR detector 111, a third IR detector 112, a fourth IR detector 113, a fifth IR detector 114 and the movable frame 13 connect together and the detection direction is toward the center. The IR detectors can be IR temperature radiation scopes using a cooling or room-temperature type linear array IR detector. The wavelength detected by the linear array IR detector ranges between 3 $\mu$m and 6 $\mu$m or 8 $\mu$m and 14 $\mu$m. When the object 12 is disposed within the movable frame 13, the first IR detector 11, the second IR detector 111, the third IR detector 112, the fourth IR detector 113 and the fifth IR detector 114 receive temperature signals radiated from the object 12 at a certain height. The received data are converted into electrical signals and output.

Figure 2:
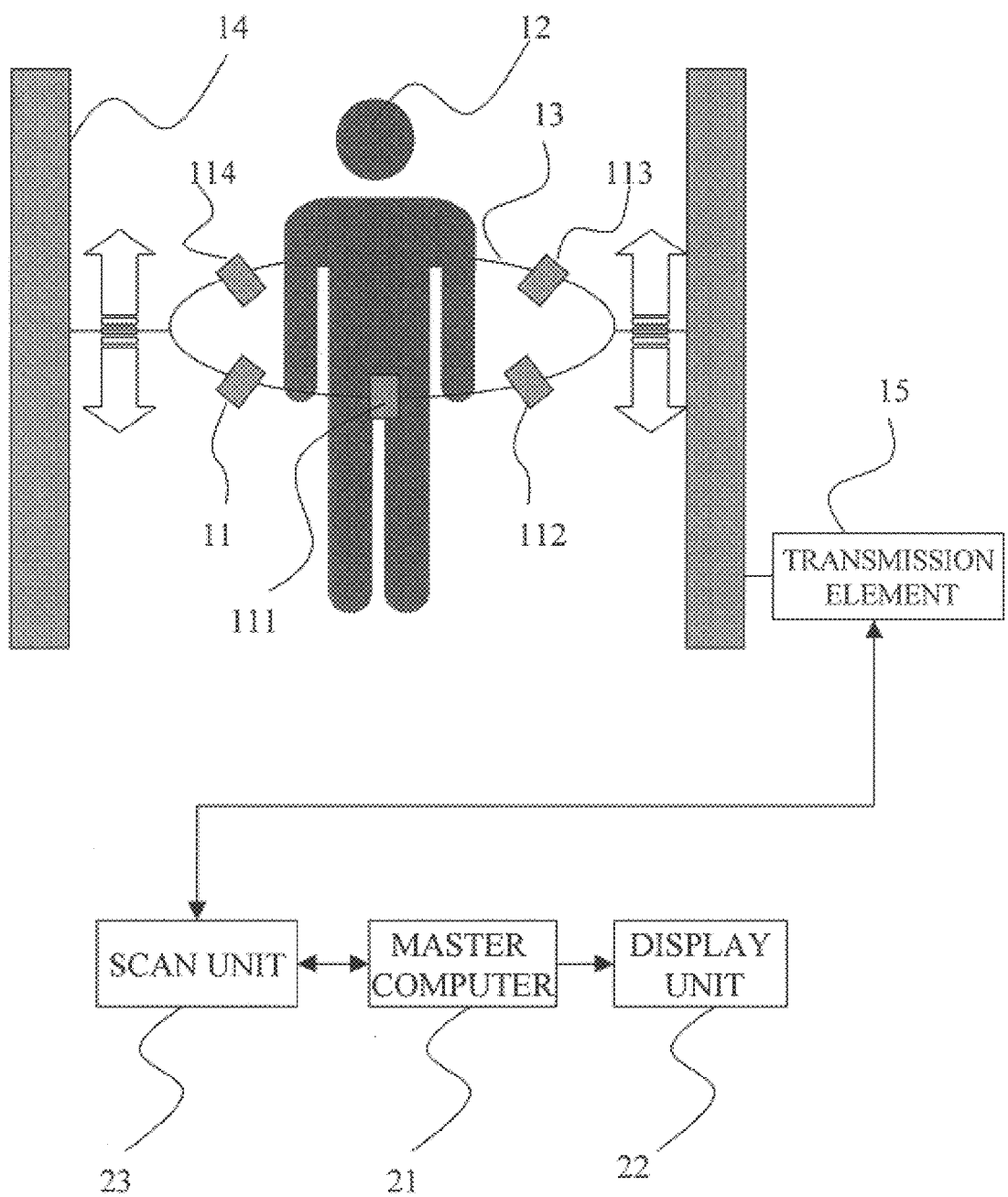
FIG. 2 is a schematic plan view of the disclosed IR 3D scanning system.
Figure 3:
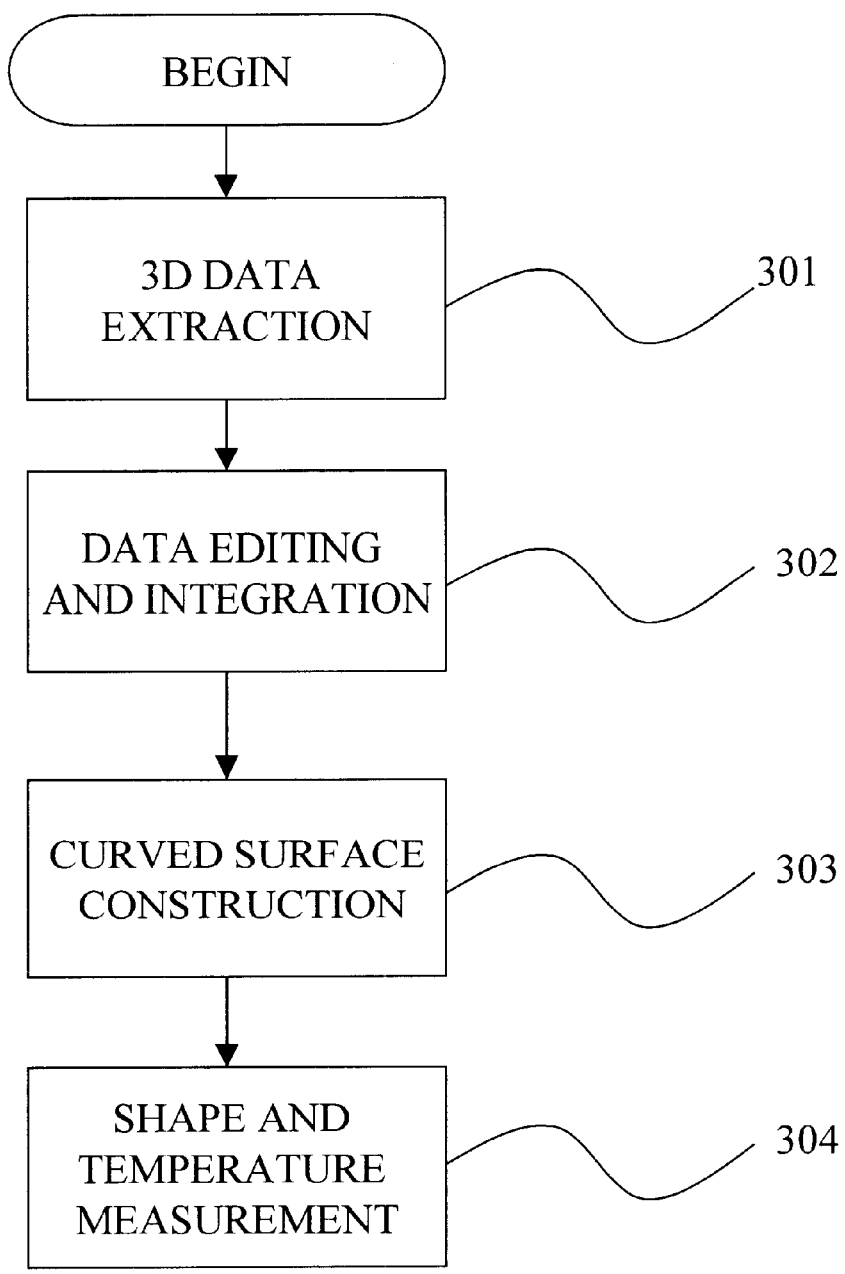
FIG. 3 is an action flow chart of an embodiment of the disclosed IR 3D scanning system.

Please refer to FIG. 2, which is a schematic front view of the disclosed IR 3D scanning system. With reference to FIG. 3 for the action flow chart of the invention at the same time, in addition to the IR detecting mechanism, the IR 3D scanning system further comprises: a master computer 21, which receives and processes signals sent out from the IR detecting mechanism; a movable frame 13, whose peripheral connects to the axial pillars 14 and a transmission element 15; a scan unit 23, which receives the command from the master computer 21 to control the action of the transmission element 15 so that the movable frame 13 moves ups and downs along the axial pillars 14 to adjust the position. The IR detectors 11, 111, 112, 113 114 can thus extract temperature information from different heights. When the object 12 is disposed within the movable frame 13, the thermal radiation from the object will give the first IR detector 11, the second IR detector 111, the third IR detector 112, the fourth IR detector 113 the fifth IR detector 114 information about the temperature of the object 12 opposite to them. When the movable frame moves ups and downs, the IR detectors can measure the thermal radiation data from the object from different heights (step 301). The measured data are then sent to the master computer to be processed by software to search for the corresponding points of the signals detected by the detectors, to calculate the 3D coordinates thereof, and to edit and integrate the data according to the continuity of consecutive points (step 302). The system then starts to reconstruct the 3D curved surface (step 303). This procedure can use polygons to construct the 3D surface of the object. Once the 3D surface is constructed, it is smoothed to obtain the 3D shape of the object. Finally, the temperature distribution is tagged onto the 3D shape of the object (step 304). The above procedures are processed by the master computer connecting to a display unit 22 so that the manipulation states and results can be displayed.

Besides, in the disclosed embodiment, if the IR detectors are IR temperature radiation scopes of surface array IR detectors, it can take whole thermal images around the human body, then there is no need to use the scan unit to control the transmission element 15 to move the movable frame in order to obtained data at different heights.

Effects of the Invention

According to the disclosed IR 3D scanning system, medical staff can analyze the human body biological state according to the 3D human shape and its temperature distribution constructed by the scanning system. The system can be applied in other purposes such as analyses and examinations of the 3D shapes and temperature distributions of objects.

Certain variations would be apparent to those skilled in the art, which variations are considered within the spirit and scope of the claimed invention.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. An infrared (IR) scanning system for performing 3D temperature sensing and 3D shape construction of an object, comprising:

an IR detecting mechanism containing a plurality of IR detectors for detecting radiation energy from the object in different angles and converting the radiation energy so measured into an electrical signal; and a signal decoding mechanism for receiving the electrical signal, editing and integrating the signal into data of a 3D profile curved surface and a corresponding temperature distribution of the object;

wherein the IR detecting mechanism further comprises a movable device connected to the plurality of IR detectors to adjust scanning positions of the plurality of IR detectors around the object, the plurality of IR detectors and the movable device are arranged such that a 3D geometrical model of the object can be directly reconstructed when the movable device moves along the object; and the signal decoding mechanism comprises a computer and a processing software capable of converting the signal detected by the plurality of IR detectors into temperature data and calculating, integrating, and editing the data according to the scanning positions of the plurality of IR detectors to simultaneously form the 3D geometrical model and the corresponding temperature distribution of the object.

2. The IR 3D scanning system of claim 1, wherein the movable device a movable frame and an axial pillar.

3. The IR 3D scanning system of claim 2, wherein the movable device further contains a transmission element combining with the axial pillar for driving and controlling the motion of the movable frame on the axial pillar.

4. The IR 3D scanning system of claim 1, wherein the IR detector is a linear array IR radiation scope.

5. The IR 3D scanning system of claim 4, wherein the linear array IR radiation scope has a detectable wavelength ranging between 3 $\mu$m and 6 $\mu$m.

6. The IR 3D scanning system of claim 4, wherein the linear array IR radiation scope has a detectable wavelength ranging between 8 $\mu$m and 14 $\mu$m.

7. The IR 3D scanning system of claim 4, wherein the linear array IR radiation scope is a cooling type linear array IR radiation scope.

8. The IR 3D scanning system of claim 4, wherein the linear array IR radiation scope is a room-temperature type linear array IR radiation scope.

9. The IR 3D scanning system of claim 1 which further comprising a transmission element for moving the movable device and a scan unit for controlling the action of the transmission element.

10. The IR 3D scanning system of claim 1 further comprising a display unit which displays in images the messages contained in the data output from the signal decoding mechanism that contain both the 3D profile data of the object and its temperature distribution.

11. The IR 3D scanning system of claim 1, wherein the IR detector is a surface IR radiation scope.

12. The IR 3D scanning system of claim 11, wherein the surface IR radiation scope has a detectable wavelength ranging between 3 $\mu$m and 6 $\mu$m.

13. The IR 3D scanning system of claim 11, wherein the surface IR radiation scope has a detectable wavelength ranging between 8 $\mu$m and 14 $\mu$m.

14. The IR 3D scanning system of claim 11, wherein the surface IR radiation scope is a cooling type surface IR radiation scope.

15. The IR 3D scanning system of claim 11, wherein the surface IR radiation scope is a room-temperature type surface IR radiation scope.

* * * * *